(12) United States Patent
Liu et al.

(10) Patent No.: US 7,919,480 B2
(45) Date of Patent: Apr. 5, 2011

(54) POLYMERS HAVING COVALENTLY BOUND ANTIBIOTIC AGENTS

(75) Inventors: Hongbo Liu, Hillsborough, NJ (US); Xintian Ming, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 974 days.

(21) Appl. No.: 11/743,815

(22) Filed: May 3, 2007

(65) Prior Publication Data
US 2008/0275230 A1 Nov. 6, 2008

(51) Int. Cl.
*A61K 31/717* (2006.01)
*C07H 15/20* (2006.01)

(52) U.S. Cl. .................. 514/54; 514/57; 536/13.6

(58) Field of Classification Search .......... 514/54, 514/57; 536/13.6
See application file for complete search history.

(56) References Cited

U.S. PATENT DOCUMENTS

| 4,810,567 | A | 3/1989 | Calcaterra et al. | |
|---|---|---|---|---|
| 5,128,326 | A * | 7/1992 | Balazs et al. | 514/54 |
| 6,033,719 | A | 3/2000 | Keogh | |
| 6,866,859 | B2 | 3/2005 | Trogolo et al. | |
| 2001/0049422 | A1 | 12/2001 | Phaneuf et al. | |
| 2005/0192547 | A1 | 9/2005 | Modak et al. | |
| 2005/0249695 | A1 | 11/2005 | Tiller et al. | |
| 2006/0024357 | A1 | 2/2006 | Carpenter et al. | |

FOREIGN PATENT DOCUMENTS

| EP | 1424086 | 6/2004 |
|---|---|---|
| FR | 2342740 | 9/1977 |
| GB | 2404920 | 2/2005 |
| JP | 60214728 A * | 10/1985 |
| WO | WO 90/15628 | 12/1990 |
| WO | WO 2005/016972 | 2/2005 |
| WO | WO 2007/014087 | 2/2007 |

OTHER PUBLICATIONS

Cera, C. et al, 'Anthracycline Antibiotics Supported on Water-Soluble Polysaccharides Synthesis and Physiochemical Characterization' International Journal of Biological Macromolecules' vol. 10, No. 2 (1988) pp. 66-74.

Deng, A. et al 'Study on Determination of Gentamicin by Enhanced Chemiluminescent Immunoassay' Journal of West China University of Medical Sciences vol. 24, No. 1 (1993) pp. 101-103.

International Search Report re: PCT/US2008/062181 dated Aug. 20, 2008.

* cited by examiner

*Primary Examiner* — Shaojia Anna Jiang
*Assistant Examiner* — Everett White
(74) *Attorney, Agent, or Firm* — Roberts Mlotkowski Safran & Cole, P.C.

(57) ABSTRACT

An antimicrobial composition comprising: a complex of a polysaccharide covalently bonded with an antibiotic. A medical device having an antimicrobial composition comprising: a complex of an oxidized regenerated cellulose covalently bonded with gentamicin.

9 Claims, 5 Drawing Sheets

Structure of Gentamicin

Gentamicin $C_1$    $R_1 = R_2 = CH_3$
Gentamicin $C_2$    $R_1 = CH_3, R_2 = H$
Gentamicin $C_{1a}$    $R_1 = R_2 = H$

Covalent Attachment of Gentamicin to ORC

Covalent attachment of ONAMER® M to ORC

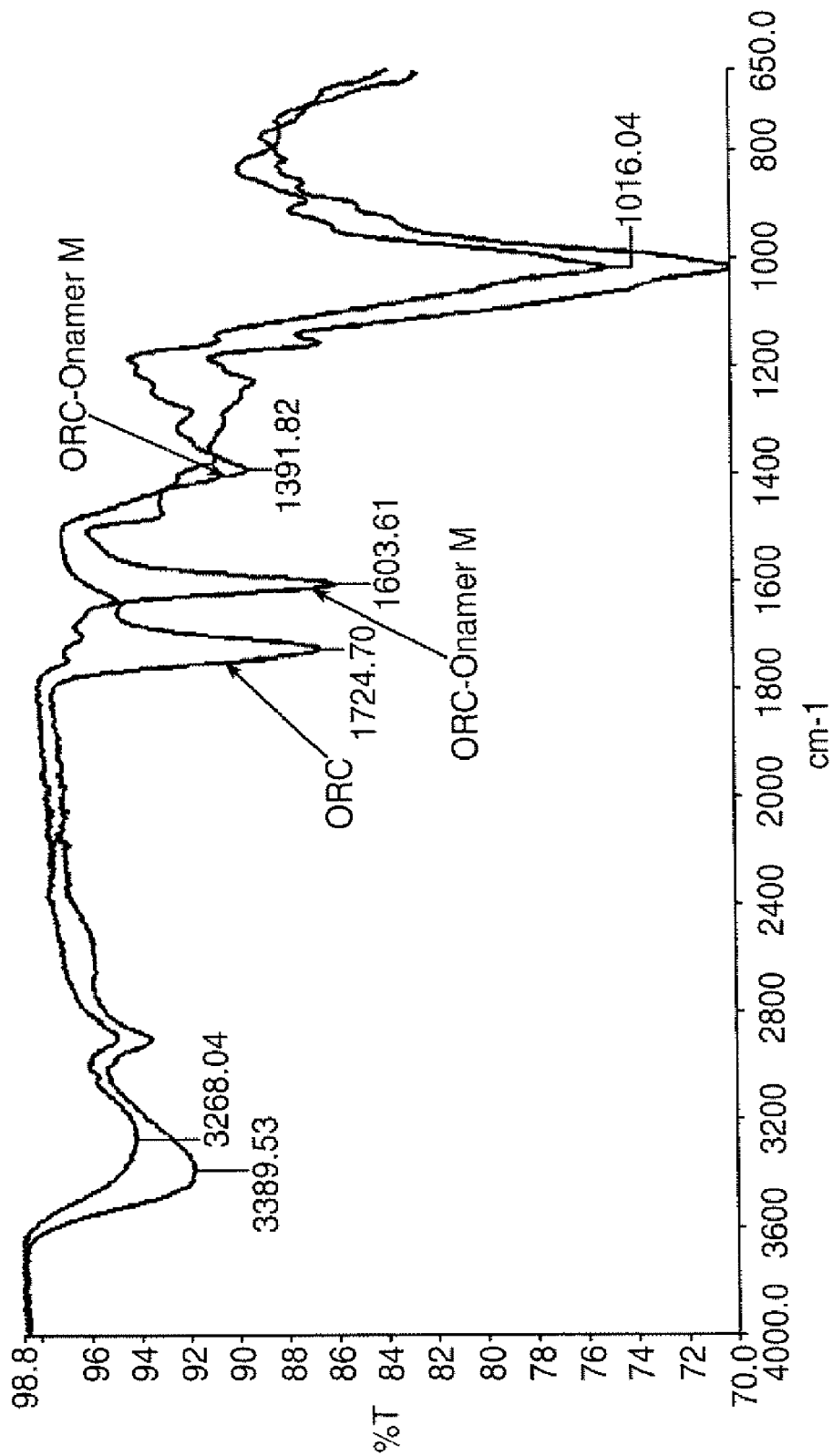

POLYMERS HAVING COVALENTLY BOUND ANTIBIOTIC AGENTS

FIELD OF THE INVENTION

The present invention relates generally to antimicrobial composition comprising polymers having covalently bound antibiotic agents and their use for making medical devices. More specifically the invention relates to antimicrobial composition comprising polysaccharides having covalently bound antibiotic agents. Further, the present invention relates to antimicrobial composition comprising oxidized regenerated cellulose (ORC) having covalently bound gentamicin which may be used alone or in combination with medical devices. The present invention also relates to medical devices utilizing such polymers having covalently bound antibiotic agents.

BACKGROUND OF THE INVENTION

Whenever a medical device is used in a surgical setting, a risk of infection is created. The risk of infection dramatically increases for invasive or implantable medical devices, such as intravenous catheters, arterial grafts, intrathecal or intracerebral shunts and prosthetic devices, which create a portal of entry for pathogens while in intimate contact with body tissues and fluids. The occurrence of surgical site infections is often associated with bacteria that colonize on the medical device. For example, during a surgical procedure, bacteria from the surrounding atmosphere may enter the surgical site and attach to the medical device. Bacteria can use the implanted medical device as a pathway to surrounding tissue. Such bacterial colonization on the medical device may lead to infection and morbidity and mortality to the patient.

A number of methods for reducing the risk of infection associated with invasive or implantable medical devices have been developed that incorporate antimicrobial agents into the medical devices. Such devices desirably provide effective levels of antimicrobial agent while the device is being used. For example, medical devices may contain antibiotics such as β-lactam antibiotics, polypeptides and quinolones. However, medical devices containing an antibiotic can suffer loss of efficacy resulting from the gradual release of the antibiotic and subsequently, producing sub-lethal concentration of such antibiotic. This sub-lethal concentration of antibiotic would select antibiotic-resistant bacteria. For instance, although β-Lactam antibiotics are known to be efficacious against *S. aureus*, the bacterial species that is believed to be the most common cause of surgical infections, these antibiotics are ineffective against antibiotic-resistant bacteria such as MRSA (methicillin-resistant *Staphylococcus aureus*) and MRSE (methicillin-resistant *Staphylococcus epidermidis*).

One potential solution to this problem is to use a combination of antibiotics and polymeric substrate to immobilize the antibiotics. In particular, it is beneficial if the polymeric substrate is covalently bonded with the antibiotic agent.

US20050192547A1 disclosed an approach for preparing anti-infective polymer-containing medical articles by treatment of the medical articles with a mixed solution of antibiotics and antiseptics. Antimicrobial activities were demonstrated by zone of inhibition (ZOI) experiments. By combination of various antibiotics and antiseptics inhibition to a range of bacteria can be achieved. However, the disclosed approach is solely based on physical absorption or deposition of the agents onto the medical articles. It is obvious that the activity provided is short-termed due to the absence of the covalent bond between the device and the antibiotics. Also, this approach may post potential risk of selecting antibiotic-resistant bacteria.

WO2005016972 A1 describes antimicrobial polymeric materials comprising a polymer linked to a positively charged moiety via a carboxyl group and the processes for the production of such antimicrobial compounds and uses thereof. Once again, the release of antibiotics is not immobilized due to the lack of covalent bonding.

There have been no reports to date on the use of a combination of polysaccharide having covalently bounded antibiotic agents. Therefore, there is a need for polysaccharides having covalently bound antibiotic agents that exhibit sustained and long-term antimicrobial efficacy.

SUMMARY OF THE INVENTION

The present invention is directed to an antimicrobial composition comprising a complex of a polysaccharide covalently bonded with at least one antibiotic agent.

More specifically, described herein is an antimicrobial composition comprising a complex of a polysaccharide covalently bonded with at least one antibiotic agent, wherein the polysaccharide is oxidized regenerated cellulose; and wherein the antibiotic agent is gentamicin.

DETAILED DESCRIPTION

The present invention provides an antimicrobial composition comprising a complex of a polysaccharide covalently bonded with at least one antibiotic agent. In one embodiment, the antimicrobial composition comprises a complex of a polysaccharide covalently bonded with at least one antibiotic agent, wherein the polysaccharide is oxidized regenerated cellulose (ORC). The complex typically comprises from about 0.1 wt. % to about 20 wt. % of the antibiotic agent.

The invention provides an effective way of immobilization of antibiotics to prevent the colonization of microorganisms on medical devices. In case of ORC with covalently immobilized gentamicin, a highly bactericidal material can be prepared.

The term "complex" as used herein refers to an intimate mixture at the molecular scale, preferably with ionic or covalent bonding between the antibiotic agent and the polysaccharide. The polysaccharide preferably comprises a carboxyl group-containing polysaccharide. Preferred polysaccharides are selected from the group consisting of carboxyl group-containing celluloses, modified starches, oxidized regenerated cellulose, chitosans, guar gums, glycans, galactans, glucans, xanthan gums, alginic acids, polymannuric acids, hyaluronic acids, polyglycosuronic and polyguluronic acids, mannans, dextrins, cyclodextrins and mixtures thereof, as well as other synthetically carboxylated or naturally occuring carboxylated polysaccharides, which may be linear or branched. The polysaccharides may be a furanosan or pyranosan associated with proteins, lipids, or other molecules, and may include algal, plant, bacterial and mucopolysaccharides, glycogen, pectin, glycoproteins, and glycolipids. Hyaluronic acid, gellan, xanthan, succinoglycan, pectin, oxidized regenerated cellulose, chondroitan sulphate, heparan sulphate, dermatan are preferred examples of carboxylated polysaccharides. Oxidized regenerated cellulose is most preferred.

Oxidized cellulose is produced by the oxidation of cellulose, for example, with dinitrogen tetraoxide. This process converts primary alcohol groups on the saccharide residues to carboxylic acid group, forming uronic acid residues within the cellulose chain. The preferred oxidized cellulose oxidized regenerated cellulose (ORC) prepared by oxidation of a regenerated cellulose, such as rayon. It has been known for some time that ORC has haemostatic properties. ORC has been available as a haemostatic product called SURGICEL (Registered Trade Mark of Johnson & Johnson Medical, Inc.) since 1950. This product is produced by the oxidation of a knitted rayon material.

Figure 2:
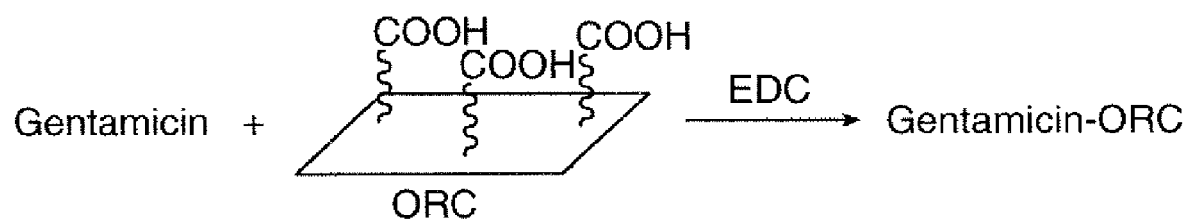

According to the present invention, an antibiotic is to be immobilized by covalent chemical bonding onto a device to achieve antimicrobial activity in a well-defined manner as shown in FIG. 2.

The covalent attachment of the antibiotics is done in a way that the antimicrobial activities of these agents are maintained effective despite of the chemical bonding. The effectiveness of this approach was demonstrated by covalent attachment of gentamicin onto oxidized regenerated cellulose (ORC). The antimicrobial activity of such modified ORC was confirmed. Covalently immobilization of antibiotics provides a way of minimizing bacteria resistance against the agents and longer lasting activity as compared to their free forms.

ORC with covalently attached antibiotics, such as gentamicin, has shown significantly enhanced antimicrobial activities against a wide range of bacteria. Gentamicin was covalently attached to the ORC's carboxylic acid by carbodiimide coupling reaction. Antimicrobial activities of such treated ORC were observed to be greater and long-lasting as compared to ORC treated alone with gentamicin solution without chemical reaction.

Gentamicin was covalently attached to ORC through carbodiimide coupling reaction. The product was washed extensively before subjected to antimicrobial activity tests. The loading of gentamicin onto the ORC was estimated at ~12%. The treated ORC showed the loss of carboxylic acid functionality and newly formed amide functionality as evidenced by FT-IR analysis.

The newly formed immobilized covalently bonded ORC-Gentamicin (ORC-GM-CVB) demonstrates significant in-vitro antimicrobial efficacy. As described in the examples below, log reduction assay showed 2 to 5 orders of magnitude reduction in bacterial counts. Untreated ORC showed none reduction in bacterial counts under the same condition.

In another aspect, the present invention includes an article of manufacture that is a medical device that comprises the antimicrobial compositions described herein. In one embodiment, the antimicrobial composition can be used to form an article or a portion of the article, for example by spinning, molding, casting, or extrusion.

The antimicrobial composition can be utilized to manufacture a medical device including, but not limited to a fiber, mesh, powder, microspheres, flakes, sponge, foam, fabric, nonwoven, woven mat, a film, suture anchor device, suture, staple, surgical tacks, clips, plate and screw, drug delivery device, adhesion prevention barrier, and tissue adhesive.

The medical device may be composed of one or more of the antimicrobial compositions of the present invention, alone or in combination with other polymeric components.

While the following examples demonstrate certain embodiments of the invention, they are not to be interpreted as limiting the scope of the invention, but rather as contributing to a complete description of the invention.

Example 1 (Inventive)

Preparation of ORC-Gentamicin (ORC-GM-CVB) Compound

Materials

Figure 1:
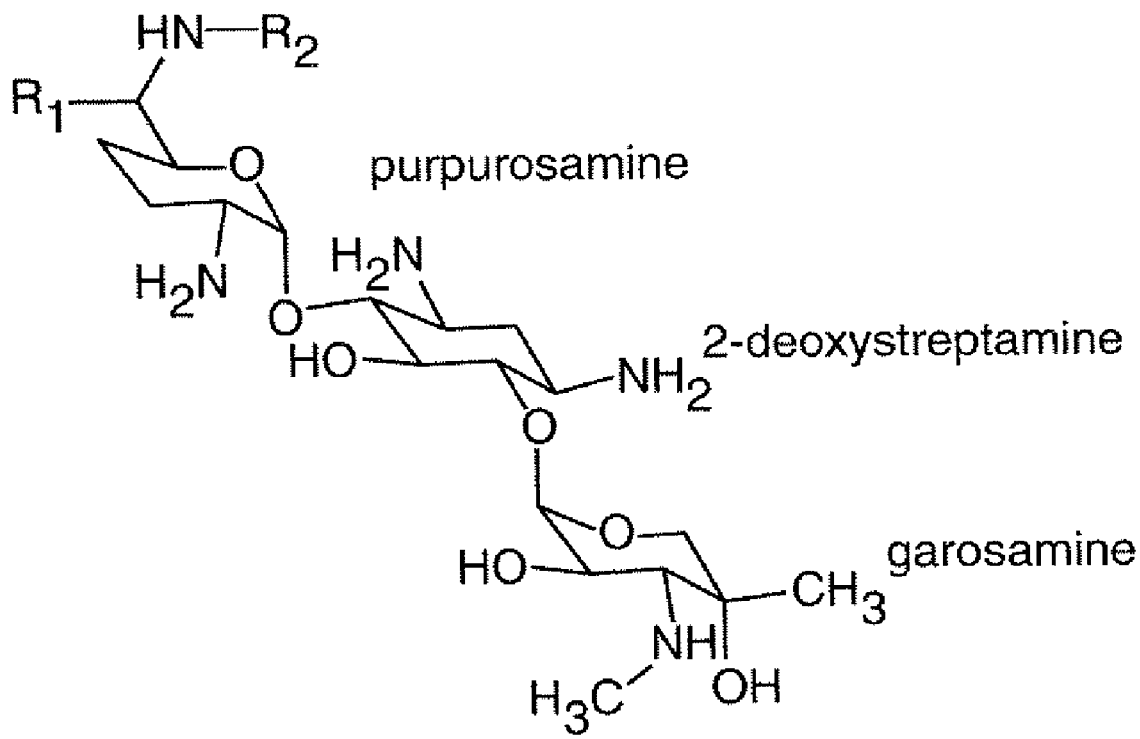
FIG. 1. Structure of Gentamicin
FIG. 2. Covalent Attachment of Gentamicin to ORC
FIG. 3. Comparison of FT-IR of untreated and treated ORC and Gentamicin
FIG. 4. Covalent attachment of ONAMER® M to ORC
FIG. 5. Comparison of FT-IR of untreated and treated ORC with ONAMER® M

All materials were purchased from Sigma-Aldrich and used as received with the exception of oxidized regenerated cellulose (ORC) fabric, which is available from Ethicon, Inc., under the tradename Interceed®. Gentamicin was acquired in sulfate form from Sigma-Aldrich as mixtures of analogs as shown in FIG. 1.

Procedure

The synthesis is outlined in FIG. 2.

ORC fabric was cut into 1" strip weighing 0.25 g. The cut ORC strip was dried under vacuum at room temperature overnight. The dried ORC strip was placed into Gentamicin solution (5 ml) in a 20 ml vial. 0.080 g 1-Ethyl-3-(3-dimethylaminopropyl)-carbodiimide (EDC) was added and the reaction vial was sealed under $N_2$ atmosphere. The reaction vial was left on a shaker at room temperature overnight.

ORC fabric was retrieved from the reaction mixture, rinsed with copious running deionized (DI) water, submerged in 50 ml DI water for 30 min and 50 ml methanol for 30 min on a shaker. The treated ORC fabric was dried under vacuum for 2 h. 0.28 g of slightly yellow colored treated ORC fabric was obtained. FT-IR was used to compare the treated and untreated ORC samples.

Figure 3:
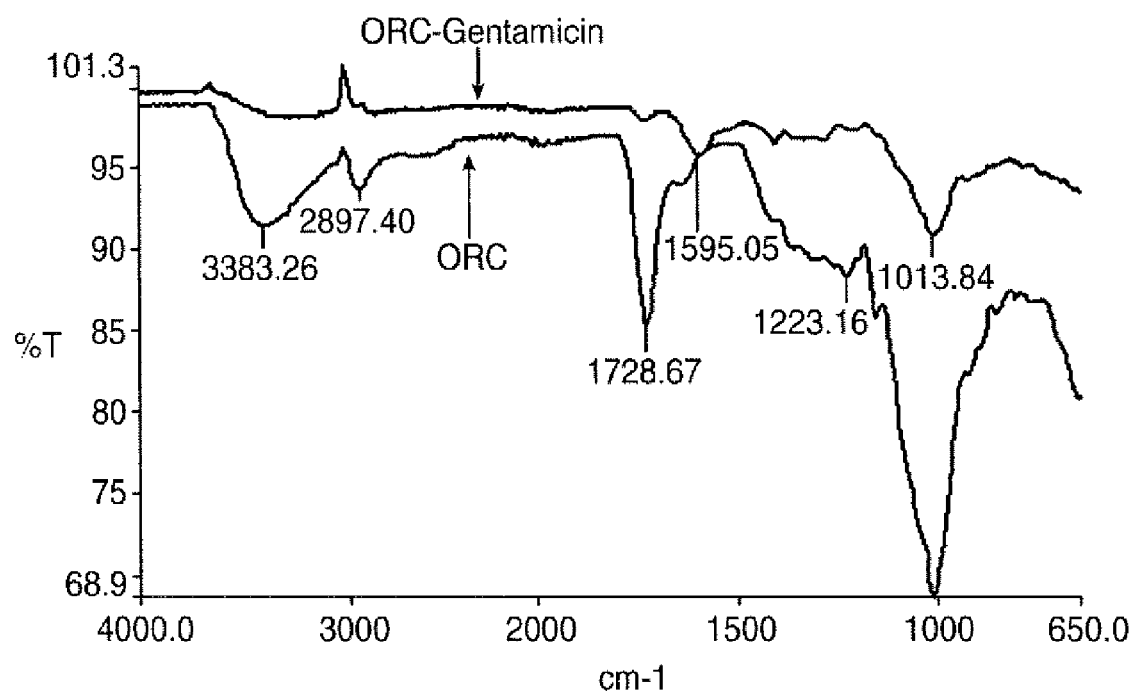

In FIG. 3, the FT-IR signals at 3383 $cm^{-1}$ (carboxylic acid proton) and 1728 $cm^{-1}$ (carboxylic acid carbonyl) for the untreated ORC indicated the presence of free carboxylic acid functionalities. After the chemical reaction of ORC with Gentamicin the signals at 3383 $cm^{-1}$ and 1728 $cm^{-1}$ disappeared while a new signal appeared at 1595 $cm^{-1}$ which is an indication for the newly formed amide bond between ORC carboxylic acid functionality and Gentamicin's amine functionality.

The above observation verified the successful covalent attachment of Gentamicin to the ORC.

Example 2 (Inventive)

The following study was conducted to demonstrate that the covalently bond Gentamicin maintained the antibacterial efficacy (table 1).

Two samples were used for the study, as follows:
1. Untreated ORC fabric
2. ORC-GM-CVB: ORC fabric with covalently bound Gentamicin prepared according to example 1

For result in table 1, test articles were tested for their in vitro efficacy by log reduction assay. To demonstrate the efficacy of covalent bond GM, the test articles were extracted in saline to remove free gentamicin before use. The test articles were squares of about 4.0 mg/piece and were extracted in 40 ml/item of sterile saline at 37° C. with shaking (100 rpm) for 1 hour for two consecutive times. Efficacy of the test articles after the extractions was evaluated by log reduction assay.

In the log reduction assay, the test articles were challenged with about 1-2×10e4 CFU bacteria on the surface of the test articles for one hour. To facilitate the test of efficacy on surface of the test articles with covalent bound gentamicin, the inoculum was delivered in 10 ul/item, the small volume relative to the test articles allowed complete absorption of the inoculum by the test articles such that the inoculum localized on surfaces of the test articles. The inoculum was prepared in 20× potassium phosphate buffer, which maintained pH of the test articles close to neutral. The antimicrobial efficacy of ORC at neutral pH will be minimized, so that the log reduction would indicate the antibacterial efficacy of Gentamicin rather than ORC. After the challenge, the test article was immersed in saline with shaking to remove survival bacteria and the survival bacteria were measured by plate count. The plate count were conducted in trypticase soy agar and incubated at 37° C. for 24 hours.

Data in Table 1 showed that ORC with covalently bond gentamicin (ORC-GM-CVB) demonstrated good in vitro efficacy of 2.8 log reduction after two consecutive extractions while the untreated ORC fabric showed no log reduction under the same testing condition. This result indicated that gentamicin was covalently bond to ORC fabric and maintain its antibacterial efficacy.

TABLE 1

Efficacy of ORC with covalent bound Gentamicin (ORC-GM-CVB)

| Sample | S. aureus | | E. coli | |
| --- | --- | --- | --- | --- |
|  | log CFU | log reduction* | log CFU | log reduction |
| Inoculum | 4.1 | n/a | 4.2 | n/a |
| ORC Control | 4.1 | 0 | 4.2 | 0 |
| ORC-GM-CVB | 1.8 | 2.3 | 1.4 | 2.8 |

*log reduction = log CFU inoculum − log CFU treated sample

Example 3 (Comparative)

Covalent Attachment of ONAMER® M to ORC

Materials

All materials unless otherwise specified were purchased from Sigma-Aldrich and used as received. ONAMER® M (POLYQUATERNIUM 1) was acquired from Stephen Company, Maywood, N.J. (lot #5572-c) as 32% aqueous solution and used as received. Oxidized regenerated cellulose (ORC) fabric was obtained from Ethicon, Inc., under the tradename Interceed®.

Procedure

Figure 4:
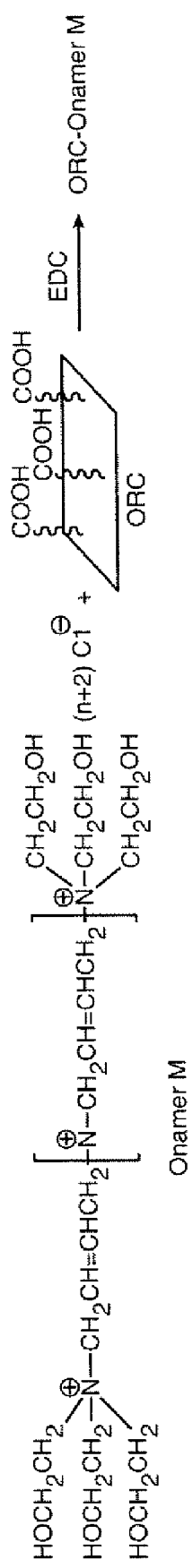

The synthesis is outlined in FIG. 4.

ORC fabric was cut into 1" strip weighing 0.25 g. The cut ORC strip was dried under vacuum at room temperature over night.

The dried ORC strip was placed into ONAMER® M solution (40 ml) in a 100 ml RBF. 0.32 g 1-Ethyl-3-(3-dimethylaminopropyl)-carbodiimide (EDC) was mixed with 5 ml water and added drop-wise to the reaction mixture through a glass pipette. The reaction mixture was capped with $N_2$ and left on a shaker at room temperature overnight.

ORC piece was retrieved from the reaction mixture, rinsed with copious running DI water, soaked in 150 ml water in beaker for 30 min and 100 ml methanol for 30 min with stirring. The treated ORC fabric was dried under vacuum for 2 h.

1.07 g of slightly yellow colored treated ORC was obtained after drying. The amount of ONAMER® M (ONM) covalently attached to the ORC is about 7%. FT-IR was used to compare treated and untreated ORC samples.

In FIG. 5, the FT-IR data confirmed the formation of the covalent bond between ORC and ONM as indicated by the signal at 1603 $cm^{-1}$.

Example 4 (Comparative)

The following study demonstrates that ONAMER® M (ONM) covalently bound to ORC lost the antibacterial efficacy (Table 2). Sample of ONM covalently bound to ORC (ORC-ONM-CV) from example 3 were tested for its in vitro efficacy by log reduction assay. In the log reduction assay, the test articles (squares of about 4.0 mg/piece) were challenged with about 1-2×10e4 CFU bacteria on the surface of the test articles for one hour. To facilitate the test of efficacy on surface of the test articles with covalent bound ONM, the inoculum was delivered in 10 ul/item, the small volume relative to the test articles allowed complete absorption of the inoculum by the test articles such that the inoculum localized on surfaces of the test articles. The inoculum was prepared in 20× potassium phosphate buffer, which maintained pH of the test articles close to neutral. The antimicrobial efficacy of ORC at neutral pH will be minimized, so that the log reduction would indicate the antibacterial efficacy of ONM rather than ORC. After the challenge, the test article was immersed in saline with shaking to remove survival bacteria and the survival bacteria were measured by plate count. The plate counts were conducted in trypticase soy agar and incubated at 37° C. for 24 hours. A positive ONM control was included in this assay to demonstrate that ONM in free form do have efficacy against the challenge bacteria.

TABLE 2

Efficacy of ORC with covalently bound ONAMER® M (ONM)

| Sample* | S. aureus ATCC 6538 | |
| --- | --- | --- |
|  | log CFU | log reduction |
| Inoculum | 4.5 | n/a |
| ORC | 4.5 | 0 |
| ORC-ONM-CV 560 ug ONM bond to ORC) | 4.5 | 0 |
| ONM control (100 ug ONM in free form on paper disc) | 0.3 | 4.2 |

*Log reduction = log CFU of inoculum − log CFU of treated (the three samples below inoculum)

What is claimed is:

1. An antimicrobial composition comprising a complex of oxidized regenerated cellulose covalently bonded with gentamicin.

2. The antimicrobial composition of claim 1, wherein the oxidized regenerated cellulose and the gentamicin are bound with an amide bond.

3. The antimicrobial composition of claim 1, wherein the gentamicin is incorporated at a level from 0.1 to about 20 wt %.

4. The antimicrobial composition of claim 3, wherein the gentamicin is incorporated at a level of about 12 wt %.

5. A medical device comprising an antimicrobial composition comprising a complex of oxidized regenerated cellulose covalently bonded with gentamicin.

6. The medical device of claim 5, wherein the oxidized regenerated cellulose and the gentamicin are bound with an amide bond.

7. The medical device of claim 5, wherein the gentamicin is incorporated at a level from 0.1 to about 20 wt %.

8. The medical device of claim 7, wherein the gentamicin is incorporated at a level of about 12 wt %.

9. The medical device of claim 5, wherein the antimicrobial composition is in the form of fibers, mesh, powders, microspheres, flakes, sponge, foam, fabric, a nonwoven fabric, a woven mat, a film, a suture anchor device, a suture, a staple, surgical tacks, clips, a plate and screw, an adhesion prevention barrier, or a tissue adhesive.

* * * * *